United States Patent
Ding

(10) Patent No.: US 10,626,413 B2
(45) Date of Patent: Apr. 21, 2020

(54) NUCLEIC ACID VECTOR

(71) Applicant: Enyu Ding, Durham, NC (US)

(72) Inventor: Enyu Ding, Durham, NC (US)

( * ) Notice: Subject to any disclaimer, the term of this patent is extended or adjusted under 35 U.S.C. 154(b) by 54 days.

(21) Appl. No.: 15/505,617

(22) PCT Filed: Jan. 15, 2016

(86) PCT No.: PCT/US2016/013588
§ 371 (c)(1),
(2) Date: Feb. 22, 2017

(87) PCT Pub. No.: WO2017/123242
PCT Pub. Date: Jul. 20, 2017

(65) Prior Publication Data
US 2017/0233761 A1 Aug. 17, 2017

(51) Int. Cl.
| | |
|---|---|
| C07H 21/04 | (2006.01) |
| C12N 15/00 | (2006.01) |
| C12N 15/63 | (2006.01) |
| C12N 15/85 | (2006.01) |
| C12N 15/64 | (2006.01) |
| C12N 15/67 | (2006.01) |
| A61K 39/00 | (2006.01) |
| C07K 14/535 | (2006.01) |
| A01K 67/00 | (2006.01) |

(52) U.S. Cl.
CPC .............. *C12N 15/85* (2013.01); *A61K 39/00* (2013.01); *C07K 14/535* (2013.01); *C12N 15/64* (2013.01); *C12N 15/67* (2013.01); *C12N 2800/107* (2013.01); *C12N 2830/50* (2013.01); *C12N 2830/60* (2013.01)

(58) Field of Classification Search
CPC ..... C12N 15/85; C12N 15/67; C12N 2830/50
See application file for complete search history.

(56) References Cited

U.S. PATENT DOCUMENTS

| | | | |
|---|---|---|---|
| 2002/0102546 A1 | 8/2002 | Nolan | |
| 2003/0104625 A1 | 6/2003 | Cheng | |
| 2007/0082400 A1* | 4/2007 | Healey | C12N 5/0639 435/459 |
| 2007/0083334 A1 | 4/2007 | Mintz et al. | |
| 2010/0048679 A1* | 2/2010 | Garren | A61K 39/0008 514/44 R |
| 2010/0266546 A1 | 10/2010 | Ramachandra et al. | |
| 2013/0078275 A1 | 3/2013 | Tao | |
| 2013/0274129 A1 | 10/2013 | Katzen et al. | |
| 2014/0227237 A1 | 8/2014 | June et al. | |
| 2014/0243399 A1 | 8/2014 | Schrum et al. | |
| 2015/0050302 A1 | 2/2015 | Thess | |

FOREIGN PATENT DOCUMENTS

| | | |
|---|---|---|
| CN | 1690207 A | 11/2005 |
| CN | 101270367 A | 9/2008 |

OTHER PUBLICATIONS

Phua KK, Staats HF, Leong KW, Nair SK. Intranasal mRNA nanoparticle vaccination induces prophylactic and therapeutic antitumor immunity. Sci Rep. Jun. 4, 2014;4:5128. doi: 10.1038/srep05128.
Pruitt SK, Boczkowski D, de Rosa N, Haley NR, Morse MA, Tyler DS, Dannull J, Nair S. Enhancement of anti-tumor immunity through local modulation of CTLA-4 and GITR by dendritic cells. Eur J Immunol. Dec. 2011;41(12):3553-63. doi: 10.1002/eji.201141383. Epub Oct. 26, 2011.
Hoerr I, Obst R, Rammensee HG, Jung G. In vivo application of RNA leads to induction of specific cytotoxic T lymphocytes and antibodies. Eur J Immunol. Jan. 2000;30(1):1-7.
Rittig SM, Haentschel M, Weimer KJ, Heine A, Muller MR, Brugger W, Horger MS, Maksimovic O, Stenzl A, Hoerr I, Rammensee HG, Holderried TA, Kanz L, Pascolo S, Brossart P. Intradermal vaccinations with RNA coding for TAA generate CD8+ and CD4+ immune responses and induce clinical benefit in vaccinated patients. Mol Ther. May 2011;19(5):990-9. doi: 10.1038/mt.2010.289. Epub Dec. 28, 2010.
Kreiter S, Vormehr M, van de Roemer N, Diken M, Lower M, Diekmann J, Boegel S, Schrörs B, Vascotto F, Castle JC, Tadmor AD, Schoenberger SP, Huber C, Türeci Ö, Sahin U. Mutant MHC class II epitopes drive therapeutic immune responses to cancer. Nature. Apr. 30, 2015;520(7549):692-6. doi: 10.1038/nature14426. Epub Apr. 22, 2015.

* cited by examiner

*Primary Examiner* — Quang Nguyen

(57) ABSTRACT

The present invention provides a nucleic acid vector referred to as pVec constructed through molecular biotechnologies. pVec contains CMV enhancer/promoter, T7 promoter, 5'UTR, MCS, 3'UTR, poly A (120A)-TTATT, BGH poly (A) signal, kanamycin resistance gene and pUC origin, etc. So pVec can be used as a vector for both DNA vaccines or therapeutic drugs and mRNA vaccines or mRNA therapeutic drugs. The 5'UTR, 3'UTR and poly A (120A)-TTATT of pVec can be added to the 5' and 3' ends of the in vitro transcribed mRNA respectively and further stabilize the transcribed mRNA. The present invention also provides the constructed pVec-GM-CSF, pVec-hIL-12 and pVAX1-hIL-12, which are used for evaluating the benefits of pVec.

5 Claims, 1 Drawing Sheet

Specification includes a Sequence Listing.

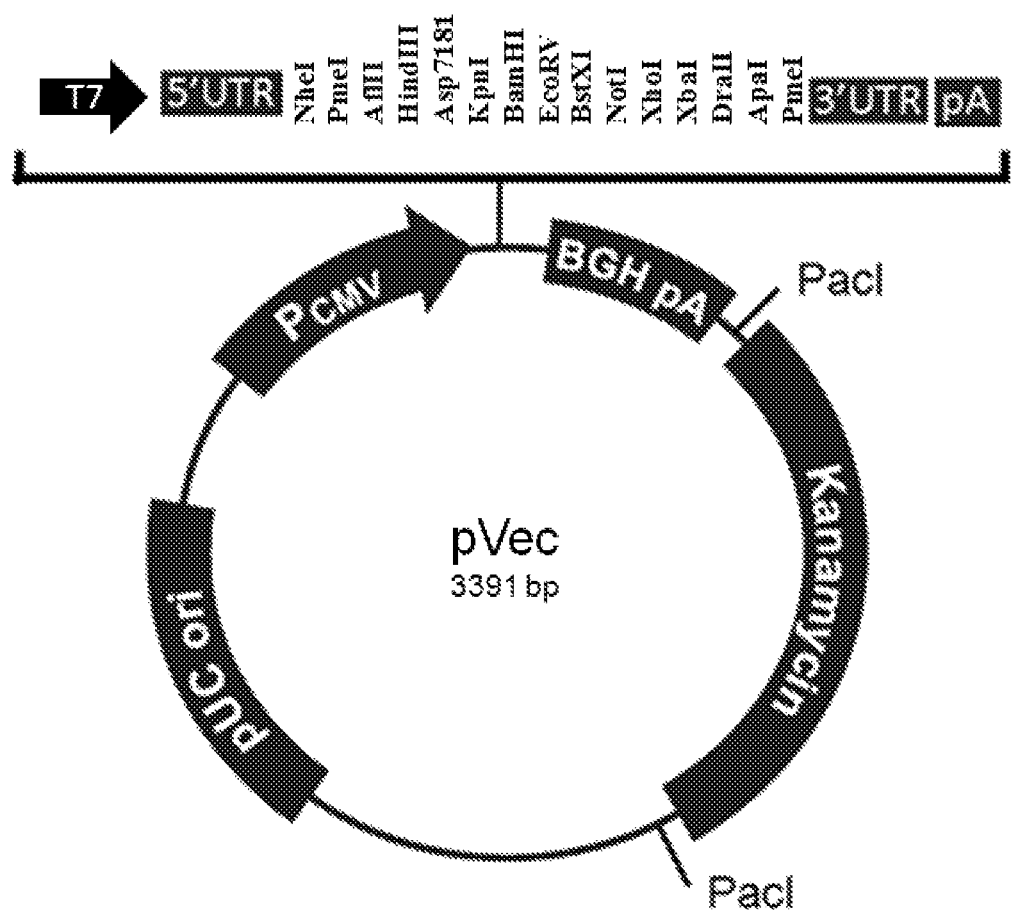

SEQUENCE LISTING

<160> NUMBER OF SEQ ID NOS: 30

<210> SEQ ID NO 1
<211> LENGTH: 33
<212> TYPE: DNA
<213> ORGANISM: Artificial Sequence
<220> FEATURE:
<223> OTHER INFORMATION: Synthesized

<400> SEQUENCE: 1
accggtaaaa tcgataaacc gcggaaaact agt                                    33

<210> SEQ ID NO 2
<211> LENGTH: 79
<212> TYPE: DNA
<213> ORGANISM: Artificial Sequence
<220> FEATURE:
<223> OTHER INFORMATION: Synthesized
<220> FEATURE:
<221> NAME/KEY: Primer
<222> LOCATION: (1)..(79)

<400> SEQUENCE: 2
acgtgggccc gtttaaacac cggtaaaatc gataaaccgc ggaaaactag tccgctgatc       60
agcctcgact gtgccttct                                                   79

<210> SEQ ID NO 3
<211> LENGTH: 35
<212> TYPE: DNA
<213> ORGANISM: Artificial Sequence
<220> FEATURE:
<223> OTHER INFORMATION: Synthesized
<220> FEATURE:
<221> NAME/KEY: primer
<222> LOCATION: (1)..(35)

<400> SEQUENCE: 3
tatacaagct cccgggagct ttttgcaaaa gccta                                  35

<210> SEQ ID NO 4
<211> LENGTH: 42
<212> TYPE: DNA
<213> ORGANISM: Artificial Sequence
<220> FEATURE:
<223> OTHER INFORMATION: Synthesized

<400> SEQUENCE: 4
ggaaaaaaaa aaaaaaaaaa aaaaaaaaaa aaaaaaaaaa aa                          42

<210> SEQ ID NO 5
<211> LENGTH: 40
<212> TYPE: DNA
<213> ORGANISM: Artificial Sequence
<220> FEATURE:
<223> OTHER INFORMATION: Synthesized

<400> SEQUENCE: 5
aaaaaaaaaa aaaaaaaaaa aaaaaaaaaa aaaaaaaaaa                             40

<210> SEQ ID NO 6
<211> LENGTH: 46
<212> TYPE: DNA
<213> ORGANISM: Artificial Sequence
<220> FEATURE:
<223> OTHER INFORMATION: Synthesized

<400> SEQUENCE: 6
aaaaaaaaaa aaaaaaaaaa aaaaaaaaaa aaaaaaaaaa ttatta    46

<210> SEQ ID NO 7
<211> LENGTH: 70
<212> TYPE: DNA
<213> ORGANISM: Artificial Sequence
<220> FEATURE:
<223> OTHER INFORMATION: Synthesized

<400> SEQUENCE: 7
ctagtaataa tttttttttt tttttttttt tttttttttt tttttttttt    60
tttttttttt    70

<210> SEQ ID NO 8
<211> LENGTH: 64
<212> TYPE: DNA
<213> ORGANISM: Artificial Sequence
<220> FEATURE:
<223> OTHER INFORMATION: Synthesized

<400> SEQUENCE: 8
tttttttttt tttttttttt tttttttttt tttttttttt tttttttttt tttttttttt    60
ccgc    64

<210> SEQ ID NO 9
<211> LENGTH: 125
<212> TYPE: DNA
<213> ORGANISM: Artificial Sequence
<220> FEATURE:
<223> OTHER INFORMATION: Synthesized
<220> FEATURE:
<221> NAME/KEY: polyA_site
<222> LOCATION: (1)..(120)

<400> SEQUENCE: 9
aaaaaaaaaa aaaaaaaaaa aaaaaaaaaa aaaaaaaaaa aaaaaaaaaa aaaaaaaaaa    60
aaaaaaaaaa aaaaaaaaaa aaaaaaaaaa aaaaaaaaaa aaaaaaaaaa aaaaaaaaaa    120
ttatt    125

<210> SEQ ID NO 10
<211> LENGTH: 89
<212> TYPE: DNA
<213> ORGANISM: Homo sapiens

<400> SEQUENCE: 10
cgatagctcg ctttcttgct gtccaatttc tattaaaggt tcctttgttc cctaagtcca    60
actactaaac tgggggatat tatgaaggg    89

<210> SEQ ID NO 11
<211> LENGTH: 52
<212> TYPE: DNA
<213> ORGANISM: Homo sapiens

<400> SEQUENCE: 11
ccttgagcat ctggattctg cctaataaaa aacatttatt ttcattgccc gc    52

<210> SEQ ID NO 12
<211> LENGTH: 88
<212> TYPE: DNA
<213> ORGANISM: Homo sapiens

<400> SEQUENCE: 12
gggcaatgaa ataaaatgtt ttttattagg cagaatccag atgctcaagg cccttcataa    60
tatcccccag tttagtagtt ggacttag                                       88

<210> SEQ ID NO 13
<211> LENGTH: 49
<212> TYPE: DNA
<213> ORGANISM: Homo sapiens

<400> SEQUENCE: 13
ggaacaaagg aacctttaat agaaattgga cagcaagaaa gcgagctat                49

<210> SEQ ID NO 14
<211> LENGTH: 83
<212> TYPE: DNA
<213> ORGANISM: Homo sapiens

<400> SEQUENCE: 14
ccggtagctc gcttgtccaa tttctattaa aggttccttt gttccctaag tccaactact    60
aaactggggg atattatgaa ggg                                            83

<210> SEQ ID NO 15
<211> LENGTH: 50
<212> TYPE: DNA
<213> ORGANISM: Homo sapiens

<400> SEQUENCE: 15
ccttgagcat ctggattctg cctaataaaa aacatttatt ttcattgcat                50

<210> SEQ ID NO 16
<211> LENGTH: 88
<212> TYPE: DNA
<213> ORGANISM: Homo sapiens

<400> SEQUENCE: 16
cgatgcaatg aaaataaatg tttttttatta ggcagaatcc agatgctcaa ggcccttcat   60
aatatccccc agtttagtag ttggactt                                       88

<210> SEQ ID NO 17
<211> LENGTH: 43
<212> TYPE: DNA
<213> ORGANISM: Homo sapiens

<400> SEQUENCE: 17
agggaacaaa ggaaccttta atagaaattg gacaagcgag cta                      43

<210> SEQ ID NO 18
<211> LENGTH: 127
<212> TYPE: DNA
<213> ORGANISM: Homo sapiens
<220> FEATURE:
<221> NAME/KEY: 3'UTR
<222> LOCATION: (1)..(127)

<400> SEQUENCE: 18
agctcgcttg tccaatttct attaaaggtt cctttgttcc ctaagtccaa ctactaaact    60
gggggatatt atgaagggcc ttgagcatct ggattctgcc taataaaaaa catttatttt   120
cattgca                                                             127

<210> SEQ ID NO 19
<211> LENGTH: 265

```
<212> TYPE: DNA
<213> ORGANISM: Artificial Sequence
<220> FEATURE:
<223> OTHER INFORMATION: Synthesized
<220> FEATURE:
<221> NAME/KEY: 3'UTR
<222> LOCATION: (1)..(265)

<400> SEQUENCE: 19
agctcgcttg tccaatttct attaaaggtt cctttgttcc ctaagtccaa ctactaaact      60 ggggatatt  atgaagggcc ttgagcatct ggattctgcc taataaaaaa catttatttt    120
cattgcatcg atagctcgct ttcttgctgt ccaatttcta ttaaaggttc ctttgttccc    180
taagtccaac tactaaactg ggggatatta tgaagggcct tgagcatctg gattctgcct    240
aataaaaaac atttattttc attgc                                          265

<210> SEQ ID NO 20
<211> LENGTH: 396
<212> TYPE: DNA
<213> ORGANISM: Artificial Sequence
<220> FEATURE:
<223> OTHER INFORMATION: Synthesized
<220> FEATURE:
<221> NAME/KEY: 3'UTR-polyA(120A)-TTATT
<222> LOCATION: (1)..(396)

<400> SEQUENCE: 20
agctcgcttg tccaatttct attaaaggtt cctttgttcc ctaagtccaa ctactaaact      60 ggggatatt  atgaagggcc ttgagcatct ggattctgcc taataaaaaa catttatttt    120
cattgcatcg atagctcgct ttcttgctgt ccaatttcta ttaaaggttc ctttgttccc    180
taagtccaac tactaaactg ggggatatta tgaagggcct tgagcatctg gattctgcct    240
aataaaaaac atttattttc attgcccgcg gaaaaaaaaa aaaaaaaaaa aaaaaaaaaa    300
aaaaaaaaaa aaaaaaaaaa aaaaaaaaaa aaaaaaaaaa aaaaaaaaaa aaaaaaaaaa    360
aaaaaaaaaa aaaaaaaaaa aaaaaaaaaa attatt                              396

<210> SEQ ID NO 21
<211> LENGTH: 75
<212> TYPE: DNA
<213> ORGANISM: Artificial Sequence
<220> FEATURE:
<223> OTHER INFORMATION: Synthesized

<400> SEQUENCE: 21
ctagattgga ccctcgtaca gaagctaata cgactcacta tagggaaata agagagaaaa      60
gaagagtaag aagaa                                                      75

<210> SEQ ID NO 22
<211> LENGTH: 28
<212> TYPE: DNA
<213> ORGANISM: Artificial Sequence
<220> FEATURE:
<223> OTHER INFORMATION: Synthesized

<400> SEQUENCE: 22
atataagagc caccgctagc gtttaaac                                        28

<210> SEQ ID NO 23
<211> LENGTH: 76
<212> TYPE: DNA
<213> ORGANISM: Artificial Sequence
<220> FEATURE:
```

<223> OTHER INFORMATION: Synthesized

<400> SEQUENCE: 23
ttaagtttaa acgctagcgg tggctcttat atttcttctt actcttcttt tctctcttat    60
ttccctatag tgagtc                                                    76

<210> SEQ ID NO 24
<211> LENGTH: 27
<212> TYPE: DNA
<213> ORGANISM: Artificial Sequence
<220> FEATURE:
<223> OTHER INFORMATION: Synthesized

<400> SEQUENCE: 24
gtattagctt ctgtacgagg gtccaat                                        27

<210> SEQ ID NO 25
<211> LENGTH: 84
<212> TYPE: DNA
<213> ORGANISM: Artificial Sequence
<220> FEATURE:
<223> OTHER INFORMATION: Synthesized
<220> FEATURE:
<221> NAME/KEY: 5'UTR
<222> LOCATION: (1)..(84)

<400> SEQUENCE: 25
ttggaccctc gtacagaagc taatacgact cactataggg aaataagaga gaaagaaga     60 gtaagaagaa atataagagc cacc                                           84

<210> SEQ ID NO 26
<211> LENGTH: 89
<212> TYPE: DNA
<213> ORGANISM: Artificial Sequence
<220> FEATURE:
<223> OTHER INFORMATION: Synthesized
<220> FEATURE:
<221> NAME/KEY: Primer
<222> LOCATION: (1)..(89)

<400> SEQUENCE: 26
acgtgaagac aatagcaggc atgctgggga tgcggtgggc tctatggctt ctttaattaa    60
actgggcggt tttatggaca gcaagcgaa                                      89

<210> SEQ ID NO 27
<211> LENGTH: 45
<212> TYPE: DNA
<213> ORGANISM: Artificial Sequence
<220> FEATURE:
<223> OTHER INFORMATION: Synthesized
<220> FEATURE:
<221> NAME/KEY: Primer
<222> LOCATION: (1)..(45)

<400> SEQUENCE: 27
acgttcatga ttaattaagc ggatacatat ttgaatgtat ttaga                    45

<210> SEQ ID NO 28
<211> LENGTH: 3391
<212> TYPE: DNA
<213> ORGANISM: Artificial Sequence
<220> FEATURE:
<223> OTHER INFORMATION: Synthesized

<400> SEQUENCE: 28

-continued

```
gctgcttcgc gatgtacggg ccagatatac gcgttgacat tgattattga ctagttatta      60
atagtaatca attacggggt cattagttca tagcccatat atggagttcc gcgttacata     120
acttacggta aatggcccgc ctggctgacc gcccaacgac ccccgcccat tgacgtcaat     180
aatgacgtat gttcccatag taacgccaat agggactttc cattgacgtc aatgggtgga     240
gtatttacgg taaactgccc acttggcagt acatcaagtg tatcatatgc caagtacgcc     300
ccctattgac gtcaatgacg gtaaatggcc cgcctggcat tatgcccagt acatgacctt     360
atgggacttt cctacttggc agtacatcta cgtattagtc atcgctatta ccatggtgat     420
gcggttttgg cagtacatca atgggcgtgg atagcggttt gactcacggg gatttccaag     480
tctccacccc attgacgtca atgggagttt gttttggcac caaaatcaac gggactttcc     540
aaaatgtcgt aacaactccg ccccattgac gcaaatgggc ggtaggcgtg tacggtggga     600
ggtctatata agcagagctc tctggctaac tagagaaccc actgcttact ggcttatcga     660
aattaatacg actcactata gggagaccca agctggctag attggaccct cgtacagaag     720
ctaatacgac tcactatagg gaaataagag agaaagaag agtaagaaga atataagag      780 ccaccgctag cgtttaaact taagcttggt accgagctcg gatcctgcag atatccagca     840
cagtggcggc cgctcgagtc tagagggccc gtttaaacac cggtagctcg cttgtccaat     900
ttctattaaa ggttcctttg ttccctaagt ccaactacta aactggggga tattatgaag     960
ggccttgagc atctggattc tgcctaataa aaaacatttta ttttcattgc atcgatagct    1020
cgctttcttg ctgtccaatt tctattaaag gttcctttgt tccctaagtc caactactaa    1080
actgggggat attatgaagg gccttgagca tctggattct gcctaataaa aaacatttat    1140
tttcattgcc gcggaaaaa aaaaaaaaaa aaaaaaaaaa aaaaaaaaaa aaaaaaaaaa      1200
aaaaaaaaaa aaaaaaaaaa aaaaaaaaaa aaaaaaaaaa aaaaaaaaaa aaaaaaaaaa     1260
aaaaaaaaaa aaaaattatt actagtccgc tgatcagcct cgactgtgcc ttctagttgc    1320
cagccatctg ttgtttgccc ctcccccgtg ccttccttga ccctggaagg tgccactccc    1380
actgtccttt cctaataaaa tgaggaaatt gcatcgcatt gtctgagtag gtgtcattct    1440
attctggggg gtggggtggg gcaggacagc aaggggagg attgggaaga caatagcagg    1500
catgctgggg atgcggtggg ctctatggct tctttaatta aactgggcgg ttttatggac    1560
agcaagcgaa ccggaattgc cagctggggc gccctctggt aaggttggga agccctgcaa    1620
agtaaactgg atggctttct cgccgccaag gatctgatgg cgcaggggat caagctctga    1680
tcaagagaca ggatgaggat cgtttcgcat gattgaacaa gatggattgc acgcaggttc    1740
tccggccgct tgggtggaga ggctattcgg ctatgactgg gcacaacaga caatcggctg    1800
ctctgatgcc gccgtgttcc ggctgtcagc gcaggggcgc ccggttcttt ttgtcaagac    1860
cgacctgtcc ggtgccctga atgaactgca agacgaggca gcgcggctat cgtggctggc    1920
cacgacgggc gttccttgcg cagctgtgct cgacgttgtc actgaagcgg gaagggactg    1980
gctgctattg ggcgaagtgc cggggcagga tctcctgtca tctcaccttg ctcctgccga    2040
gaaagtatcc atcatggctg atgcaatgcg gcggctgcat acgcttgatc cggctacctg    2100
cccattcgac caccaagcga aacatcgcat cgagcgagca cgtactcgga tggaagccgg    2160
tcttgtcgat caggatgatc tggacgaaga gcatcagggg ctcgcgccag ccgaactgtt    2220
cgccaggctc aaggcgagca tgcccgacgg cgaggatctc gtcgtgaccc atggcgatgc    2280
ctgcttgccg aatatcatgg tggaaaatgg ccgcttttct ggattcatcg actgtggccg    2340
gctgggtgtg gcggaccgct atcaggacat agcgttggct acccgtgata ttgctgaaga    2400
```

```
gcttggcggc gaatgggctg accgcttcct cgtgctttac ggtatcgccg ctcccgattc    2460
gcagcgcatc gccttctatc gccttcttga cgagttcttc tgaattatta acgcttacaa    2520
tttcctgatg cggtattttc tccttacgca tctgtgcggt atttcacacc gcatacaggt    2580
ggcacttttc ggggaaatgt gcgcggaacc cctatttgtt tattttctca aatacattca    2640
aatatgtatc cgcttaatta atcatgacca aaatccctta acgtgagttt tcgttccact    2700
gagcgtcaga ccccgtagaa aagatcaaag gatcttcttg agatcctttt tttctgcgcg    2760
taatctgctg cttgcaaaca aaaaaaccac cgctaccagc ggtggtttgt ttgccggatc    2820
aagagctacc aactcttttt ccgaaggtaa ctggcttcag cagagcgcag ataccaaata    2880
ctgtccttct agtgtagccg tagttaggcc accacttcaa gaactctgta gcaccgccta    2940
catacctcgc tctgctaatc ctgttaccag tggctgctgc cagtggcgat aagtcgtgtc    3000
ttaccgggtt ggactcaaga cgatagttac cggataaggc gcagcggtcg ggctgaacgg    3060
ggggttcgtg cacacagccc agcttggagc gaacgaccta caccgaactg agatacctac    3120
agcgtgagct atgagaaagc gccacgcttc ccgaagggag aaaggcggac aggtatccgg    3180
taagcggcag ggtcggaaca ggagagcgca cgagggagct tccaggggga aacgcctggt    3240
atctttatag tcctgtcggg tttcgccacc tctgacttga gcgtcgattt ttgtgatgct    3300
cgtcaggggg gcggagccta tggaaaaacg ccagcaacgc ggccttttta cggttcctgg    3360
gcttttgctg gccttttgct cacatgttct t                                   3391

<210> SEQ ID NO 29
<211> LENGTH: 59
<212> TYPE: DNA
<213> ORGANISM: Homo sapiens
<220> FEATURE:
<221> NAME/KEY: Primer
<222> LOCATION: (1)..(59)

<400> SEQUENCE: 29
acgtaagctt gccgccacca tggggctgca gagcctgctg ctcttgggca ctgtggcct     59

<210> SEQ ID NO 30
<211> LENGTH: 40
<212> TYPE: DNA
<213> ORGANISM: Homo sapiens
<220> FEATURE:
<221> NAME/KEY: Primer
<222> LOCATION: (1)..(40)

<400> SEQUENCE: 30
acgtctcgag tcactcctgg actggctccc agcagtcaaa                          40
```

NUCLEIC ACID VECTOR

BACKGROUND OF THE INVENTION

The present invention in the field of biotechnology relates to a nucleic acid molecule. In particular, the present invention relates to a universal nucleic acid drug vector enhancing mRNA stability and translatability.

The nucleic acid drug applies DNA and RNA as a vaccine or a therapeutic drug for prevention and treatment of diseases in clinical applications. For many years, RNA has been considered to be unstable and susceptible to degradation. Thus most research in nucleic acid drugs, in particular nucleic acid vaccines, is based on DNA vaccines. A DNA vaccine is a plasmid DNA containing a foreign antigen gene sequence. It is delivered into the host body and enters the nucleus through the cellular and nuclear membranes. In the nucleus, the delivered foreign antigen gene DNA is transcribed into mRNA, which is then transported to the cytoplasm and translated into protein by ribosomes in the cytoplasm. The expressed protein can be taken up and processed by antigen presenting cells (APCs) such as dendritic cells (DCs) into multiple epitopes, which are bound with major histocompatibility complex (MHC) in animals or human leukocyte antigen (HLA) in human and presented to T cells, further eliciting immune responses such as generating cytotoxic T lymphocytes (CTLs) and antibodies, and achieving the purpose of prevention and treatment of diseases such as cancer and viral diseases. Also the transcribed mRNA can be used as therapeutic drugs.

Conventional DNA vaccine vectors include pcDNA3.1 and pVAX1. Among them, pcDNA3.1 is banned by US Food and Drug Administration (FDA) from human clinical use because pcDNA3.1 contains an ampicillin resistance gene. Since a DNA vaccine does not easily pass through the cellular and nuclear membranes, only a few DNA molecules can enter the nucleus, making it difficult to stimulate the body and further elicit a strong immune response. Therefore, no DNA vaccine has yet been approved for human clinical use. Currently, the employed electroporation method greatly improves the transfection efficiency and the immune effect of DNA vaccines, but there are still concerns regarding whether the plasmid DNA can be integrated into the host cell's genome.

In recent years, improvements in plasmid vectors have increased the stability of the in vitro transcribed mRNA, turning our attention to mRNA drugs, especially to mRNA vaccines. pGEM4Z/GFP/A64 and pGEM4Z/OVA/A64 are constructed based on pGEM4Z/A64 vector and made as templates for producing the in vitro transcribed mRNAs, which are inoculated via the intranasal route to induce anti-tumor immunity [Phua K K, et al. Sci Rep. 2014; 4:5128]. Using pcDNA3.1-64A and pSP73-Sph/A64, several vectors containing tumor-associated antigens (TAAs), glucocorticord-induced TNFR-related protein monoclonal antibody (GITR mAb) and cytotoxic T-lymphocyte-associated protein-4 mAb (CTLA-4 mAb) are respectively constructed and used for producing the corresponding in vitro transcribed mRNAs, which are electroporated into dendritic cells (DCs). Subsequently the obtained DC-mRNA vaccines are used for enhancing anti-tumor immunity [Pruitt S K, et al. Eur J Immunol. 2011; 41(12): 3553-63]. pSpjC-βglacZβga$_n$ and pT7TSiβggfpβga$_n$ are respectively constructed, resulting in LacZ and green fluorescent protein (GFP) genes flanked by 5'-untranslated region (UTR) and 3'UTR from *Xenopus laevis* β-globin respectively [Hoerr I, et al. Eur J Immunol. 2000; 30 (1): 1-7]. The plasmid vectors containing TAAs such as mucin1 (MUC1), carcinoembryonic antigen (CEA), human epidermal growth factor receptor 2 (Her-2/neu), telomerase, survivin and melanoma-associated antigen 1 (MAGE-1) are respectively constructed utilizing pSP64-Poly (A)-EGFP-2 provided by V. F. I. Van Tendeloo and taken as templates for producing the in vitro transcribed mRNAs, which are used for anti-tumor immunity [Rittig S M, et al. Mol Ther. 2011; 19 (5): 990-9]. Also 5'top UTR is artificially synthesized and applied for increasing mRNA stability [Andreas Thess. US 20150050302 A1. Artificial nucleic acid molecules comprising a 5'top utr]. Several plasmids containing multiple mutant major histocompatibility complex (MHC) class II epitope sequences are respectively constructed using pST1-Sp-MITD-2hBgUTR-A120 and used for producing the in vitro transcribed mRNAs, which are inoculated into the body for generating personalized anti-cancer immunity [Kreiter S, et al. Nature 2015; 520 (7549): 692-6].

Among the above mentioned vectors, pGEM4Z/A64, pcDNA3.1-64A, pSP73-Sph/A64 and pSP64-Poly (A)-EGFP-2 do not have 5'UTR and 3'UTR, and contain only a short polyadenylation (poly A) tail (64A) so that the mRNA in vitro transcribed utilizing the above vectors is susceptible to degradation. Although containing 5'UTR and 3'UTR, pSpjC-βglacZβga$_n$ and pT7TSβggfβga$_n$ contain 3'UTR with only a *Xenopus laevis* β-globin so that their effect of stabilizing the in vitro transcribed mRNA is not ideal. pST1-Sp-MITD-2hBgUTR-A120 contains 3'UTR (with two β-globin) and poly A (120A), but it does not contain TTATT sequence as a terminator after poly A (120A) and its 5'UTR is not ideal. Therefore, there is still room for improvement. Other reported mRNA vaccine vectors that are not mentioned here are mostly made with minor improvements on the above plasmids.

Currently almost all the bacterial antibiotic resistance genes of plasmid vectors for generating the in vitro transcribed mRNA vaccines are ampicillin resistance genes. Before the in vitro transcribed mRNA can be deemed effective for human clinical use, it is necessary to check whether the ampicillin resistance gene remains in the final product. In addition, according to the provisions of the FDA, the plasmid vectors containing ampicillin resistance gene cannot be used as DNA vaccines for human clinical use.

SUMMARY OF THE INVENTION

The object of the present invention is to provide a universal nucleic acid drug vector enhancing mRNA stability and translatability.

To achieve the object of the present invention, the technical program used is as follows. First of all, conventional pcDNA3.1 is taken as the vector backbone and inserted with the fragment containing restriction endonuclease AgeI, ClaI, SacII and SpeI sites obtained by polymerase chain reaction (PCR) method after ApaI and PmeI sites of multiple cloning sites (MCS) of pcDNA3.1. Then the fragment containing poly A (120A) and TTATT (termination sequence) is subcloned between SacII and SpeI sites of the above vector. The fragment containing the first human β-globin 3'UTR is subcloned between ClaI and SacII sites. The fragment containing the second human β-globin 3'UTR is subcloned between AgeI and ClaI sites. Further, the fragment containing artificially designed and synthesized DNA as 5'UTR is subcloned before NheI site. Finally, pcDNA3.1-5'UTR-MCS-3'UTR-pA is constructed through the above steps.

To delete SpeI site in the MCS, the above obtained pcDNA3.1-5'UTR-MCS-3'UTR-pA is digested with BamHI and EcoRI, blunted and then self-ligated by head to tail connection, obtaining pcDNA3.1-5'UTR-MCS (no SpeI, BamHI/EcoRI)-3'UTR-pA.

To replace the ampicillin resistance gene of the above vector with a kanamycin resistance gene, the fragment containing MluI-MCS-BbsI region of pcDNA3.1-5'UTR-MCS (no SpeI, BamHI/EcoRI)-3'UTR-pA is obtained by digesting pcDNA3.1-5'UTR-MCS (no SpeI, BamHI/EcoRI)-3'UTR-pA with MluI and BbsI, and then subcloned between MluI and BbsI sites of pVAX1, obtaining pVec0-5'UTR-MCS (no SpeI, BamHI/EcoRI)-3'UTR-pA.

To conveniently replace the kanamycin resistance gene of the above vector with other non-bacterial antibiotic resistance gene in the future, the fragment containing BbsI-PacI-KanR-PacI-BspHI region obtained by PCR is subcloned into BbsI and BspHI (second BspHI) sites of pVec0-5'UTR-MCS (no SpeI, BamHI/EcoRI)-3'UTR-pA, obtaining pVec1-5'UTR-MCS (no SpeI, BamHI/EcoRI)-3'UTR-pA (with BbsI-PacI-KanR-PacI-BspHI), referred to as pVec.

In order to evaluate the benefits of pVec, the present invention also provides the constructed pVec-GM-CSF, which shows that pVec can be a DNA vaccine or drug vector as well as an mRNA vaccine or drug vector. In addition, the present invention also provides the constructed pVec-hIL-12 and pVAX1-hIL-12, which demonstrate that the in vitro transcribed mRNA generated by taking pVec-hIL-12 as a template is relatively stable and the amount of the corresponding hIL-12 expression is high.

BRIEF DESCRIPTION OF THE DRAWINGS

FIG. 1 pVec vector map
The nucleotide length of pVec: 3391 bp
CMV enhancer: bases 36-415
CMV promoter: bases 416-619
T7 promoter: bases 664-680
5'UTR: bases 702-785
Multiple cloning sites: bases 786-878
3'UTR: bases 885-1149
PolyA: bases 1156-1275
TTATT termination sequence: bases 1276-1280
BGH poly (A) signal: bases 1304-1528
Kanamycin resistance gene: bases 1709-2503
pUC origin: bases 2738-3326.

DETAILED DESCRIPTION OF THE INVENTION

The present invention provides a nucleic acid vector referred to as pVec, which is constructed using conventional molecular biotechnologies through the following steps.

Taking conventional pcDNA3.1 as a template, the fragment containing restriction endonuclease AgeI, ClaI, SacII and SpeI sites (SEQ ID NO: 1) is obtained via polymerase chain reaction (PCR) using the forward primer (SEQ ID NO: 2) and the reverse primer (SEQ ID NO: 3), subcloned after ApaI and PmeI sites of the MCS of pcDNA3.1 and transformed into top10 chemically competent E. coli cells or DH5 alpha competent cells, obtaining pcDNA3.1-MCS-ApaI-PmeI-AgeI-ClaI-SacII-SpeI.

To insert poly A (120A) tail-TTATT sequence in the vector, several synthesized oligonucleotides including polyAF1 (SEQ ID NO: 4), polyAF2 (SEQ ID NO: 5), polyAF3 (SEQ ID NO: 6), polyAR1 (SEQ ID NO: 7) and polyAR2 (SEQ ID NO: 8) are phosphorylated with T4 polynucleotide kinase (New England Biolabs, Catalog #: M0201S) at 37° C. for an hour, denatured at 94° C. for 10 minutes, annealed at room temperature for 30 minutes and ligated with T4 DNA ligase at 16° C. overnight, and then subcloned into dephosphorylated SacII and SpeI sites of pcDNA3.1-MCS-ApaI-PmeI-AgeI-ClaI-SacII-SpeI catalyzed by alkaline phosphatase, calf intestinal [(CIP), New England Biolabs, Cat #: M0290S], obtaining pcDNA3.1-MCS-ApaI-PmeI-AgeI-ClaI-SacII-poly A (120A)-TTATT-SpeI. The nucleotide sequence of the inserted poly A (120A)-TTATT sequence is as set forth in SEQ ID NO: 9.

To insert 3'UTR (from human β-globin) in the vector, the synthesized oligonucleotides including 3'UTRClaIF1 (SEQ ID NO: 10), 3'UTRClaIF2 (SEQ ID NO: 11), 3'UTRSacIIR1 (SEQ ID NO: 12) and 3'UTRSacIIR2 (SEQ ID NO: 13) are phosphorylated, denatured, annealed and ligated with T4 DNA ligase, then subcloned into dephosphorylated ClaI and SacII sites of pcDNA3.1-MCS-ApaI-PmeI-AgeI-ClaI-SacII-poly A (120 A)-TTATT-SpeI, obtaining pcDNA3.1-MCS-ApaI-PmeI-AgeI-ClaI-3'UTR (β-globin)-SacII-poly A (120 A)-TTATT-SpeI.

To insert another 3'UTR (from human β-globin) in the vector, the synthesized oligonucleotides including 3'UTRAgeIF1 (SEQ ID NO: 14), 3'UTRAgeIF2 (SEQ ID NO: 15), 3'UTRClaIR1 (SEQ ID NO: 16) and 3'UTRClaIR2 (SEQ ID NO: 17) are phosphorylated, denatured, annealed and ligated with T4 DNA ligase, and then subcloned into dephosphorylated AgeI and ClaI sites of pcDNA3.1-MCS-ApaI-PmeI-AgeI-ClaI-3'UTR (β-globin)-SacII-poly A (120 A)-TTATT-SpeI, obtaining pcDNA3.1-MCS-ApaI-PmeI-AgeI-3'UTR (β-globin)-ClaI-3'UTR (β-globin)-SacII-poly A (120 A)-TTATT-SpeI. The percentage identity between a query sequence and a subject is obtained using basic local alignment search tool (BLAST). The nucleotide sequence between AgeI and ClaI sites of the β-globin 3'UTR is identical or at least 93% identical to SEQ ID NO: 18. The nucleotide sequence of 3'UTR (2 β-globin) is identical or at least 96% identical to SEQ ID NO: 19 and the nucleotide sequence of 3'UTR-poly A (120A)-TTATT is identical or at least 96% identical to SEQ ID NO: 20.

To insert 5'UTR in the vector, the oligonucleotides including 5'UTRF1 (SEQ ID NO: 21), 5'UTRF2 (SEQ ID NO: 22), 5'UTRR1 (SEQ ID NO: 23) and 5'UTRR2 (SEQ ID NO: 24) designed and synthesized by referencing eukaryotic 18s rRNA sequence are phosphorylated, denatured, annealed and ligated with T4 DNA ligase, and then subcloned into dephosphorylated NheI and AflII sites of pcDNA3.1-MCS-ApaI-PmeI-AgeI-3'UTR (β-globin)-ClaI-3'UTR (3-globin)-SacII-poly A (120 A)-TTATT-SpeI, resulting in 5'UTR inserted before NheI and obtaining pcDNA3.1-5'UTR-MCS-ApaI-PmeI-AgeI-3'UTR (β-globin)-ClaI-3'UTR (β-globin)-SacII-poly A (120 A)-TTATT-SpeI, referred to as pcDNA3.1-5'UTR-MCS-3'UTR-pA. The nucleotide sequence of 5'UTR is as set forth in SEQ ID NO: 25.

To delete SpeI site between BamHI and EcoRI sites of the MCS, pcDNA3.1-5'UTR-MCS-3'UTR-pA is digested with BamHI and EcoRI, blunted and then self-ligated by head to tail connection, obtaining pcDNA3.1-5'UTR-MCS (no SpeI, BamHI/EcoRI)-3'UTR-pA.

To replace the ampicillin resistance gene of the vector with a kanamycin resistance gene, the fragment containing MluI-MCS-BbsI region of pcDNA3.1-5'UTR-MCS (no SpeI, BamHI/EcoRI)-3'UTR-pA is obtained by digesting pcDNA3.1-5'UTR-MCS (no SpeI, BamHI/EcoRI)-3'UTR-pA with MluI and BbsI, and then subcloned between MluI and BbsI sites of pVAX1, obtaining pVec0-5'UTR-MCS (no SpeI, BamHI/EcoRI)-3'UTR-pA.

To conveniently replace the kanamycin resistance gene of the vector with other non-bacterial antibiotic resistance genes in the future, the fragment containing BbsI-PacI-KanR-PacI-BspHI region is obtained via PCR by taking pVec0-5'UTR-MCS (no SpeI, BamHI/EcoRI)-3'UTR-pA as a template and using the forward primer (SEQ ID NO: 26) and the reverse primer (SEQ ID NO: 27), subsequently subcloned into BbsI and BspHI (second BspHI) sites of pVec0-5'UTR-MCS (no SpeI, BamHI/EcoRI)-3'UTR-pA, achieving pVec1-5'UTR-MCS (no SpeI, BamHI/EcoRI)-3'UTR-pA (with BbsI-PacI-KanR-PacI-BspHI), referred to as pVec. pVec is deposited as PTA-122648 at the American Type Culture Collection (ATCC).

The complete nucleotide sequence of pVec has been sequenced by US Genewiz Company and has identity or at least 86% identity to SEQ ID NO: 28.

The present invention provides a nucleic acid vector referred to as pVec, which contains CMV enhancer/promoter, T7 promoter, 5'UTR, MCS, 3'UTR, poly A (120A)-TTATT, bovine growth hormone (BGH) poly (A) signal, kanamycin resistance gene and pUC origin, etc. pVec having the size of 3,391 bp is relatively small so that pVec can accommodate large exogenous gene sequences. The 5'UTR sequence of pVec can be added to the 5'end of the in vitro transcribed mRNA. The 3'UTR and poly A (120A)-TTATT sequence of pVec can be added to the 3'end of the in vitro transcribed mRNA. The 5'UTR, 3'UTR and poly A (120A)-TTATT sequence of pVec can stabilize the in vitro transcribed mRNA, further for making mRNA vaccines or therapeutic drugs. Restriction endonuclease SpeI site of the MCS of pVec is deleted and another SpeI site is inserted after poly A (120A)-TTATT sequence of pVec. Therefore, it is easy to generate the linearized plasmid DNA through SpeI digestion and further produce the in vitro transcribed mRNA. pVec contains CMV enhancer/promoter, MCS, BGH poly (A) signal and kanamycin resistance gene and pUC origin so that pVec can be used as a vector for DNA vaccines or therapeutic drugs in human clinical applications. The 5'UTR, 3'UTR and poly A (120A)-TTATT sequence of pVec can be added to the 5' and 3' end of the transcribed mRNA in cells so that pVec can stabilize the transcribed mRNA better than other conventional vectors such as pcDNA3.1 and pVAX1. In addition, the kanamycin resistance gene of pVec is flanked by two restriction endonuclease PacI sites and easily replaced with other non-antibiotic resistance genes, further generating the DNA vaccine with the non-antibiotic selection gene.

Example 1: Construction and Expression of pVec-GM-CSF

Taking pCMV-SPORT6-GM-CSF [purchased from Open Biosystems, human granulocyte macrophage colony-stimulating factor (GM-CSF), GenBank accession number: BC108724] as a template, the product obtained by PCR amplification using the forward primer designed and synthesized according to Kozak sequence (the nucleotide sequence is identical or at least 81% identical to SEQ ID NO: 29) and the reverse primer (the nucleotide sequence is identical or at least 93% identical to SEQ ID NO: 30) is subcloned into HindIII and XhoI sites of pVec, which is transformed into E. coli cells (e.g., top10 chemically competent E. coli cells or DH5 alpha competent cells), obtaining pVec-GM-CSF.

pVec-GM-CSF is amplified, purified with Qiaprep spin miniprep kit (Qiagen, Cat #: 27106), and digested with restriction endonuclease SpeI, obtaining the linearized plasmid DNA. A small amount of the above SpeI cut plasmid DNA is used for detecting whether pVec-GM-CSF is completely linearized by 1% agarose gel electrophoresis. The mixture of 100 μl SpeI cut plasmid DNA reaction solution with about 500 μl Buffer PB is transferred into a spin column, centrifuging for 30 seconds and discarding the effluent (flow-through). Then 750 μl Buffer PE is added to the above spin column, centrifuging for 30 seconds and draining the effluent, centrifuging for 1 minute again. The spin column is put into a clean micro-centrifuge tube, adding 30 μl H$_2$O to the spin column, standing for 1 minute and centrifuging for 1 minute. The concentration of the purified linearized pVec-GM-CSF is checked and adjusted to 0.5 to 1 μg/l.

The in vitro transcribed GM-CSF mRNA is generated by taking the above purified linearized pVec-GM-CSF as a template and using HiScribe™ T7 High Yield RNA Synthesis Kit (New England Biolabs, Cat #: E2040S) and 3'-0-Me-m$^7$G(5')ppp(5')G RNA Cap Structure Analog (ARCA, New England Biolabs, Cat #: S1411S) through the following steps.

In detail, the following reagents are added to a 1.5 ml micro-centrifuge tube at room temperature.

| | | |
|---|---|---|
| Nuclease-free water | x μl | |
| 10 X reaction buffer | 2 μl | |
| ATP (100 mM) | 2 μl | 10 mM final |
| UTP (100 mM) | 2 μl | 10 mM final |
| CTP (100 mM) | 2 μl | 10 mM final |
| GTP (20 mM) | 2 μl | 2 mM final |
| ARCA (40 mM) | 4 μl | 8 mM final |
| Template DNA (linearized) | x μl | 1 μg |
| T7 RNA polymerase mix | 2 μl | |
| Total reaction volume | 20 μl | |

After mixing well and pulse-spinning, the above reaction tube is incubated at 37° C. for 2 hours. To remove the template DNA, 70 μl nuclease-free H$_2$O, 10 μl of 10× DNase I buffer and 2 μl DNase I (New England Biolabs, Cat #: M0303S) are added to the above reaction tube, incubating at 37° C. for 15 minutes.

Using RNeasy mini kit (Qiagen, Cat #: 74104), the in vitro transcribed GM-CSF mRNA is purified by the following steps.

About 20 to 30 μl of the above in vitro transcribed mRNA diluted with nuclease-free H$_2$O is taken and transferred into a micro-centrifuge tube (nuclease-free). 350 μl Buffer RLT containing 1% β-mercaptoethanol (β-ME) is added to the above tube. After thoroughly mixing with pipette, adding an equal volume of 70% ethanol and mixing again, the above mixture is transferred into a spin column for centrifuging and draining the effluent (flow-through). 700 μl Buffer RW1 is added to the above spin column, draining the effluent after centrifugation. 500 μl Buffer RPE is added to the above spin column, centrifuging, draining the effluent and repeating twice. After centrifuging for 1 minute, the spin column is transferred into a clean micro-centrifuge tube (nuclease-free) and 30 μl nuclease-free H$_2$O is added to the spin column, standing for 1 minute and then centrifuging. The resulting product is the purified in vitro transcribed GM-CSF mRNA. The concentration of the above mRNA is checked using a nanodrop spectrophotometer and then its quality is detected by 1% formaldehyde agarose gel electrophoresis.

pVec-GM-CSF DNA (5 μg) and the in vitro transcribed GM-CSF mRNA (5 μg) are respectively electroporated into 1×10$^6$ cells (e.g., mouse B16F10 cells or D5LacZ cells, etc.) in a 0.2 cm cuvette at the condition of 350 V and 500 μs. The above cells electroporated with the DNA or mRNA are cultured in a cell culture medium at 5% $CO_2$, 37° C. for 36 hours and the supernatants are respectively collected.

Using human GM-CSF enzyme-linked immunosorbent assay (ELISA) kit (eBioscience, Cat #: 88-8337-22), human GM-CSF expressed in the supernatant is detected by the following steps.

The ELISA plate is coated with 100 µl capture antibody diluted with 1× coating buffer at the ratio of 1:250 for each well, sealed and incubated at 4° C. overnight.

After discarding the coating solution, rinsing with wash buffer [1× phosphate-buffered saline (PBS) containing 0.05% Tween-20] 3 times, at least 1 minute each time, and patting dry, 200 µl of 1× ELISA/ELISPOT Diluent is added to each well of the above plate, incubating at room temperature for 1 hour.

After washing the plate according to the previous method, 100 µl of 1× ELISA/ELISPOT Diluent diluted standard human GM-CSF or 100 µl of the collected supernatant is added to each well of the above plate, then sealing and incubating at room temperature for 2 hours.

After washing the plate according to the previous method 3 to 5 times, 100 µl of 1× ELISA/ELISPOT Diluent diluted detection antibody is added to each well, then sealing and incubating at room temperature for 1 hour.

After washing the plate according to the above method 3 to 5 times, 100 µl of 1× ELISA/ELISPOT Diluent diluted Avidin-horseradish peroxidase (HRP) is added to each well, sealing and incubating at room temperature for 30 minutes.

After washing the plate according to the above method 5 to 7 times, 100 µl of 1× tetramethylbenzidine (TMB) solution is added to each well, then incubating at room temperature for 15 minutes.

Then 50 µl of 2 M $H_2SO_4$ stop solution is added to each well of the above plate. The concentration of human GM-CSF expressed in the cell supernatant is determined by measuring optical density (OD) value at 450 nm using a micro-plate reader.

The results show that both the cells electroporated with pVec-GM-CSF DNA and the cells with the in vitro transcribed GM-CSF mRNA can express human GM-CSF. In addition, the cells electroporated with the in vitro transcribed GM-CSF mRNA stored at room temperature for over three weeks can still express GM-CSF.

Example 2: Construction of pVec-hTL-12 and Comparing pVec-hIL-12 with pVAX1-hIL-12

Human interleukin-12 (hIL-12) gene is obtained by digesting pORF-hIL-12 G2 (InvivoGen) with SalI and NheI, and subcloned into XhoI and XbaI sites of pVec, obtaining pVec-hIL-12. Also, hIL-12 gene digested with SalI and NheI is subcloned into XhoI and XbaI sites of pVAX1 (Invitrogen), obtaining pVAX1-hTL-12.

Using the above mentioned method, pVec-hIL-12 and pVAX1-hIL-12 are respectively amplified, purified with Qiaprep spin miniprep kit (Qiagen, Cat #: 27106) and linearized by SpeI digestion, obtaining the corresponding linearized plasmid DNAs. The concentration of the resultant linearized pVec-hIL-12 and pVAX1-hIL-12 is checked and adjusted to 0.5 to 1 µg/l.

The in vitro transcribed mRNAs respectively from pVec-hIL-12 and pVAX1-hIL-12 are generated by the previous indicated method. The obtained mRNAs are respectively purified using RNeasy mini kit (Qiagen, Cat #: 74104). The concentration of the mRNAs is checked using a nanodrop spectrophotometer and their quality is detected by 1% formaldehyde agarose gel electrophoresis.

pVec-hIL-12 DNA, the in vitro transcribed hIL-12 mRNA from pVec-hIL-12, pVAX1-hIL-12 DNA and the in vitro transcribed hIL-12 mRNA from pVAX1-hIL-12 (5 µg/each) are respectively electroporated into $1\times10^6$ cells (such as mouse B16F10 cells or D5LacZ cells, etc.) in a 0.2 cm cuvette at the condition of 350 V and 500 is. The above electroporated cells are cultured in a cell growth medium at 5% $CO_2$, 37° C. for 36 hours, the supernatants of the above cells are respectively collected.

The collected supernatants are respectively used for detecting human IL-12 expression using human IL-12 ELISA kit (eBioscience, Cat #: 88-7126-88) by the previous mentioned protocol.

The ELISA plate is coated with 100 µl capture antibody diluted with 1× coating buffer at the ratio of 1:250 for each well, sealed and incubated at 4° C. overnight.

After discarding the coating solution containing capture antibody, rinsing with wash buffer (1×PBS containing 0.05% Tween-20) 3 times, at least 1 minute each time, and patting dry, 200 µl of 1× ELISA/ELISPOT Diluent is added to each well of the above plate, then incubating at room temperature for 1 hour.

According to the previous mentioned method, the above plate is washed. 100 µl of 1× ELISA/ELISPOT Diluent diluted standard human IL-12 or 100 µl of the collected supernatant is added to each well, then sealing and incubating at room temperature for 2 hours.

The plate is washed according to the previous method 3 to 5 times and 100 µl of 1× ELISA/ELISPOT Diluent diluted detection antibody is added to each well, then sealing and incubating at room temperature for 1 hour.

The plate is washed according to the above method 3 to 5 times. 100 µl of 1× ELISA/ELISPOT Diluent diluted Avidin-HRP is added to each well, then sealing and incubating at room temperature for 30 minutes.

The plate is washed according to the above method 5 to 7 times. 100 µl of 1×TMB solution is added to each well, incubating at room temperature for 15 minutes.

Then 50 µl of 2 M $H_2SO_4$ stop solution is added to each well of the above plate. Further, the concentration of human IL-12 expressed in the cell supernatant is determined by measuring OD value at 450 nm using a micro-plate reader.

The experiments show that the cells electroporated with pVec-hIL-12 DNA, the in vitro transcribed mRNA from pVec-hIL-12, pVAX1-hIL-12 DNA and the in vitro transcribed mRNA from pVAX1-hIL-12 can express hTL-12 respectively. In addition, pVec-hIL-12 as a template is used for generating the in vitro transcribed mRNA, which has good stability. The amount of hIL-12 expressed by the in vitro transcribed mRNA from pVec-hIL-12 is also higher than that of the in vitro transcribed mRNA from pVAX1-hIL-12.

The invention claimed is:

1. A pVec comprises a nucleic acid sequence that is identical to or at least 86% sequence identical to SEQ ID NO: 28, wherein said nucleic acid sequence comprises nucleotide sequences of a 5'UTR, a 3'UTR and polyA (120A)-TTATT.

2. The pVec of claim 1, wherein the nucleotide sequence between AgeI and ClaI sites of the 3'UTR is identical to or at least 93% sequence identical to SEQ ID NO: 18.

3. The pVec of claim 1, wherein the nucleotide sequence of the 3'UTR is identical to or at least 96% sequence identical to SEQ ID NO: 19.

4. The pVec of claim 1, wherein the nucleotide sequence containing the 3'UTR and polyA (120)-TTATT is identical to or at least 96% sequence identical to SEQ ID NO: 20.

5. The pVec of claim 1, wherein the pVec has the size of 3,391 base pairs to accommodate an exogenous sequence.

* * * * *